United States Patent
Spivack et al.

(10) Patent No.: US 10,792,129 B2
(45) Date of Patent: Oct. 6, 2020

(54) SOFT TISSUE IN-GROWTH OF POROUS, THREE-DIMENSIONALLY PRINTED, TRANSCUTANEOUS IMPLANTS OF VARYING MATERIAL AND PORE GEOMETRY

(71) Applicant: University of Maine System Board of Trustees, Orono, ME (US)

(72) Inventors: Kyle J. Spivack, Orono, ME (US); Anne B. Lichtenwalner, Orono, ME (US); James A. Weber, Dedham, ME (US); David J. Neivandt, Bangor, ME (US); Ian D. Dickey, Bangor, ME (US)

(73) Assignee: University of Maine System Board of Trustees, Orono, ME (US)

( * ) Notice: Subject to any disclaimer, the term of this patent is extended or adjusted under 35 U.S.C. 154(b) by 162 days.

(21) Appl. No.: 15/547,899

(22) PCT Filed: Feb. 3, 2016

(86) PCT No.: PCT/US2016/016318
§ 371 (c)(1),
(2) Date: Aug. 1, 2017

(87) PCT Pub. No.: WO2016/126789
PCT Pub. Date: Aug. 11, 2016

(65) Prior Publication Data
US 2018/0021139 A1   Jan. 25, 2018

Related U.S. Application Data

(60) Provisional application No. 62/111,308, filed on Feb. 3, 2015.

(51) Int. Cl.
*A61C 8/00* (2006.01)
*A61B 17/86* (2006.01)
(Continued)

(52) U.S. Cl.
CPC ............ *A61C 8/0012* (2013.01); *A61B 17/60* (2013.01); *A61B 17/866* (2013.01);
(Continued)

(58) Field of Classification Search
CPC ..... A61B 17/84; A61B 17/86; A61B 17/8605; A61B 17/861; A61B 17/8615;
(Continued)

(56) References Cited

U.S. PATENT DOCUMENTS

| 5,607,474 A * | 3/1997 | Athanasiou ............... A61F 2/28 623/23.71 |
| 2002/0177903 A1 * | 11/2002 | Geistlich ............... A61F 2/0077 623/23.72 |

(Continued)

FOREIGN PATENT DOCUMENTS

WO   WO-2016/126789 A1   8/2016

OTHER PUBLICATIONS

International Search Report for PCT/US2016/016318, 3 pages (Apr. 14, 2016).
Written Opinion for PCT/US2016/016318, 5 pages (Apr. 14, 2016).

*Primary Examiner* — Eric S Gibson
(74) *Attorney, Agent, or Firm* — Choate Hall & Stewart, LLP; Brian E. Reese; Meaghan E. Bychowski (57) ABSTRACT

The present invention provides, among other things, implants including a biocompatible substrate, wherein the substrate includes a plurality of pores, such as trabecular and/or dodecahedral pores, and wherein said implant is configured as a transcutaneous implant. In some embodiments, provided implants may comprise multiple layers with differing pore densities, geometries, and/or distributions.

11 Claims, 9 Drawing Sheets

A

B (51) Int. Cl.
*A61B 17/60* (2006.01)
*A61L 27/06* (2006.01)
*A61F 2/00* (2006.01)
*A61F 2/30* (2006.01)

(52) U.S. Cl.
CPC ............ *A61F 2002/0086* (2013.01); *A61F 2002/3092* (2013.01); *A61F 2002/30141* (2013.01); *A61F 2310/00023* (2013.01); *A61F 2310/00131* (2013.01); *A61F 2310/00179* (2013.01); *A61L 27/06* (2013.01)

(58) Field of Classification Search
CPC . A61B 17/862; A61B 17/8625; A61B 17/863; A61B 17/8635; A61B 17/864; A61B 17/8645; A61B 17/866; A61B 2017/8655; A61C 8/0012; A61C 8/0013; A61C 8/0016; A61F 2002/0086; A61F 2002/3092; A61F 2310/00023; A61F 2310/00131; A61F 2310/00179; A61L 2300/414; A61L 2400/18
See application file for complete search history.

(56) References Cited

U.S. PATENT DOCUMENTS

| | | | |
|---|---|---|---|
| 2005/0112397 A1* | 5/2005 | Rolfe | A61B 17/8605 428/593 |
| 2005/0232968 A1* | 10/2005 | Palmaz | A61F 2/00 424/423 |
| 2006/0073181 A1* | 4/2006 | Kuboki | A61C 8/0006 424/422 |
| 2006/0229615 A1* | 10/2006 | Abdou | A61B 17/7035 606/256 |
| 2006/0240062 A1* | 10/2006 | Hellerbrand | A61C 8/0013 424/423 |
| 2007/0202144 A1* | 8/2007 | Hellerbrand | A61B 17/866 424/423 |
| 2008/0020349 A1* | 1/2008 | Dricot | A61C 8/0012 433/174 |
| 2008/0045963 A1* | 2/2008 | Abdou | A61B 17/7032 606/86 A |
| 2009/0036908 A1* | 2/2009 | Zokol | A61B 17/60 606/151 |
| 2009/0177273 A1* | 7/2009 | Piveteau | A61F 2/82 623/1.46 |
| 2009/0215007 A1 | 8/2009 | Caterini et al. | |
| 2011/0052834 A1* | 3/2011 | Lenz | A61C 8/0013 427/535 |
| 2013/0178947 A1* | 7/2013 | Monaghan | A61L 27/56 623/23.55 |
| 2014/0058524 A1* | 2/2014 | Gray | A61F 2/2846 623/20.17 |
| 2014/0121776 A1* | 5/2014 | Hunt | A61F 2/4455 623/17.16 |
| 2014/0288650 A1* | 9/2014 | Hunt | A61F 2/447 623/16.11 |
| 2015/0032222 A1 | 1/2015 | Monaghan et al. | |
| 2015/0173797 A1* | 6/2015 | Ametani | A61F 2/2846 606/60 |
| 2016/0081807 A1* | 3/2016 | Estes | A61F 2/30756 623/14.12 |
| 2018/0021139 A1* | 1/2018 | Spivack | A61L 27/54 606/331 |

* cited by examiner

SOFT TISSUE IN-GROWTH OF POROUS, THREE-DIMENSIONALLY PRINTED, TRANSCUTANEOUS IMPLANTS OF VARYING MATERIAL AND PORE GEOMETRY

BACKGROUND

Titanium and tantalum metal implants have been used in an extensive variety of studies in the biomedical field due to their biologically inert nature. Recent developments in additive manufacturing have enabled the production of implants with highly tunable structures, including porous designs. As such it is now possible to perform systematic studies of the efficacy of porous materials; studies performed to date have largely focused on orthopedic and dental applications. Indeed, porous metal implants comprised of titanium and tantalum, for example, have been utilized for a variety of applications, such as the promotion of bone in-growth.

SUMMARY OF THE INVENTION

The present invention provides, inter alia, implants including a biocompatible substrate, wherein the substrate includes a plurality of pores, such as trabecular and/or dodecahedral pores, and wherein said implant is configured as a transcutaneous implant. In some embodiments, provided implants may comprise multiple layers with differing pore densities, geometries, and/or distributions. Existing transcutaneous implants, such as the external fixators employed in orthopedic procedures, are prone to infection and invariably require concurrent administration of antibiotics to the patient. Prior to the present invention, the development of transcutaneous implants having very low risk of infection were not thought possible. In some embodiments, unlike previous implants, provided implants do not allow for tissue growth over exterior surface of the implant (e.g., tissue ingrowth is at or below the skin surface level of a subject).

Previous studies have been conducted that demonstrated porous metal implants can facilitate the in-growth of subcutaneous soft tissue in some circumstances. Specifically, it has been demonstrated that porous blocks of tantalum successfully promoted the in-growth and attachment of fibrous tissue when implanted into the dorsal subcutaneous tissue of canines. Animal trials by Hacking et al. demonstrated that porous networks of inert metal are biocompatible and may promote soft tissue in-growth with little to no infection, and further, that tissue in-growth can occur for a variety of pore sizes.

However, with only a small number of studies focused on soft tissue in-growth in porous implants, the mechanism of soft tissue in-growth remains unclear, and knowledge of what parameters are required or desirable for the facilitation of healthy in-growth have been absent. Further, prior to the present invention, no in-vivo analyses of porous implants that are transcutaneous in nature, in which the implants penetrate through dermal layers and into the subcutaneous tissue, had been performed. Such studies are required in order to determine the potential for porous implants to promote wound healing in applications with very high rates of infection. Herein is described, for the first time, transcutaneous implants that facilitate skin in-growth and allow for formation of an effective biological seal, which reduces or prevents bacteria and foreign pathogens from migrating into the subcutaneous tissue, a common cause of infection.

The production of porous metals has previously been limited to methods such as electron beam melting (EBM), laser engineered net shaping (LENS) and selective laser melting (SLM). Such methods are complicated, slow, and have limited specific spatial resolution. Recent advances in additive manufacturing, such as three dimensional printing allow for the rapid production of highly specific, reproducible structures, in which material and geometry are very precisely controlled. In some embodiments, this approach is advantageous, as a single computer aided draft can be created and employed to produce multiple implants that possess the same geometries, but with different materials, or different geometries utilizing a single material. In the Example, additive manufacturing is employed to create trabecular and dodecahedral porous implants of both titanium and plastic. The effect of varying pore geometry and implant material in promoting in-growth of skin, subcutaneous and granular tissue was studied.

DETAILED DESCRIPTION

In some embodiments, the present invention provides implants including a biocompatible substrate, wherein the biocompatible substrate includes a plurality of pores, and wherein said implant is configured as a transcutaneous implant. In some embodiments, the pores are regular and/or substantially uniform in at least one of size and shape. In some embodiments, the regular and/or substantially uniform pores are dodecahedral. In some embodiments, the pores are irregular and/or exhibit at least two different geometries. In some embodiments, the pores exhibit a trabecular or substantially trabecular geometry.

In some embodiments, the present invention provides implants including a biocompatible substrate including a first layer and a second layer, wherein the first layer comprises a plurality of pores, and the second layer comprises a plurality of pores, and wherein the pores of the first layer have geometries and/or sizes that are different than the pores of the second layer. In some embodiments, the pores of the first layer are regular and/or substantially uniform in at least one of size and shape. In some embodiments, the pores of the second layer are regular and/or substantially uniform in at least one of size and shape. In some embodiments, the regular and/or substantially uniform pores are dodecahedral. In some embodiments, the pores of the first layer are irregular and/or exhibit at least two different geometries. In some embodiments, the pores of the second layer are irregular and/or exhibit at least two different geometries. In some embodiments, the pores exhibit a trabecular or substantially trabecular geometry. In some embodiments, provided implants comprising at least some pores with a trabecular geometry may be or comprise a highly porous foam. In some embodiments, provided implants can have more than two layers (e.g., 3, 4, 5, 6, 7, 8, 9, 10, or more).

According to various embodiments, the pores of provided implants can vary in any application appropriate way. In some embodiments, the pores may vary across a single layer of an implant in terms shape, size, or some other property or parameter. In some embodiments, pores have a diameter between 1-5,000 µm (e.g., 1-4,000 µm, 1-3,000 µm, 1-2,000 µm, 1-1,000 µm). In some embodiments, the substrate comprises titanium, tantalum, a polymer, or a ceramic material. In some embodiments, provided implants may be coated with or otherwise incorporate one or more biological agents. In some embodiments such biological agents may enhance one or more of cell ingrowth, cell viability, or cell differentiation. In some embodiments, biological agents are anti-infective agents such as anti-bacterial agents, anti-viral agents, and/or anti-fungal agents. In some embodiments, the substrate is coated with one or more growth factors.

In some embodiments, provided implants facilitate skin tissue ingrowth into at least 50% of the plurality of pores (e.g., 60%, 70%, 80%, 90%, 95%, or greater). In some embodiments, provided implants facilitate subcutaneous tissue ingrowth into at least 50% of the plurality of pores (e.g., 60%, 70%, 80%, 90%, 95%, or greater).

EXAMPLE

Figure 1:
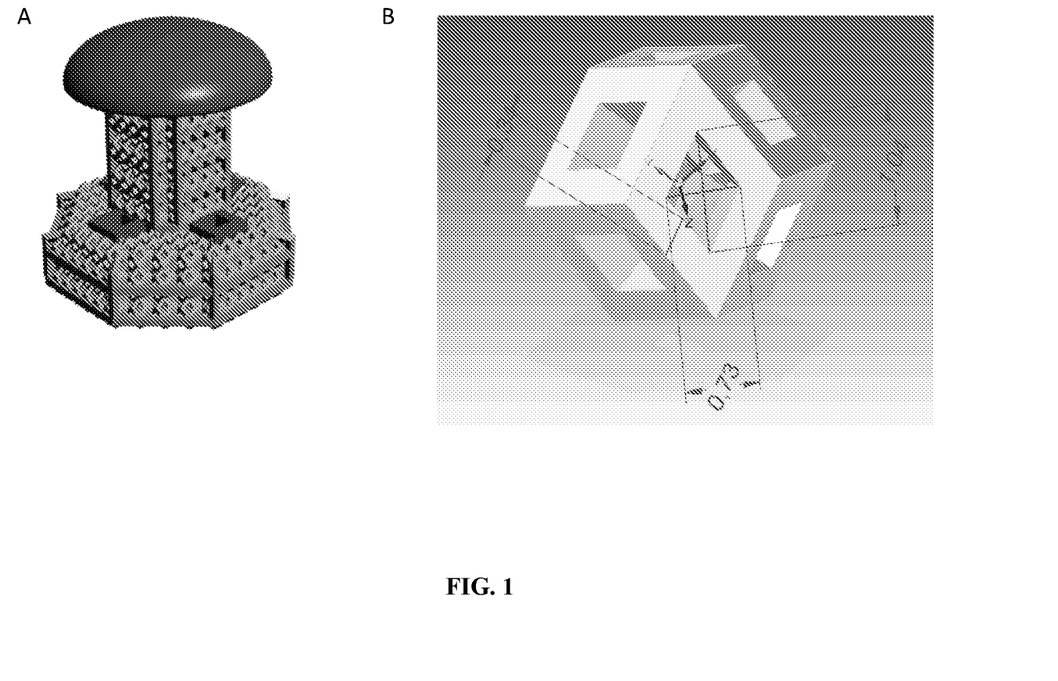
FIG. 1A-B show A) an exemplary computer aided draft of a dodecahedral porous implant; and B) an exemplary individual rhombic dodecahedral pore.

In this Example, provided implants featured a vertical post with a solid core encased in a porous network. A hemispherical cap sat atop the post, while an octagonal base comprising a solid core surrounded by a porous network sat below the post. The octagonal base harbored four reinforced suture holes. The geometry of the porous network was either trabecular in nature (employing the proprietary geometry of Stryker Corporation), or a repeating dodecahedral configuration. The rhombic dodecahedral pores each comprised 12 open faces, 14 vertices and 24 edges. Diagonal lengths across each open face were 1.04 mm and 0.73 mm. Square profile struts with widths of 0.34 mm comprised the edge of each face. Each pore had an internal volume of 3.76 mm$^3$. Individual rhombic dodecahedra were stacked via aligned faces to create a complete space filling, interconnected network. A representative computer rendered image of a dodecahedral porous implant is given in FIG. 1(a), with an individual rhombic dodecahedral pore presented in FIG. 1(b) along with relevant dimensions.

Titanium implants with both a dodecahedral geometry porous network, and separately, a trabecular geometry porous network (e.g., a highly porous foam network), were additively printed and manufactured by Stryker Corporation (Kalamazoo, Mi). Plastic implants with a dodecahedral geometry porous network were additively printed and manufactured by GROWit (Lake Forest, Calif.) and were constructed of MED610, a biocompatible PolyJet photopolymer.

Eight female New Zealand Rabbits (Charles River Laboratory, Boston, Mass.) weighing 4 to 5 kg were employed in the present study. Surgery was conducted in June and July of 2013, at the small animal facility located at The University of Maine (Orono, Me.). A surgical plane of anesthesia was induced and anesthesia was maintained during surgery using an inhalant. Rabbit's body temperatures were maintained using a pediatric surgical warming unit. Pulse rate and arterial oxygen tension were continuously monitored during surgery.

Each rabbit received four transcutaneous implants (one titanium trabecular pore geometry implant, one titanium dodecahedral pore geometry implant, and two plastic dodecahedral pore geometry implants) that were sutured into the subcutaneous tissues adjacent to the dorsal mid-line in the thoracic region. A superficial posterior approach to the subcutaneous tissues was performed through four skin incisions (one for each implant) into the skin overlying the dorsal paraspinal muscles at the level of the thorax (two incisions each approximately two cm to the left and right of the dorsal mid-line in the mid-thoracic region). Implants were placed through each of the four skin incisions so that their octagonal bases rested on the fascial layer overlying the paraspinal muscles and their vertical posts were surrounded by subcutaneous tissues and skin. The base of each implant was affixed to the muscular fascia with four absorbable sutures. The vertical post arising from the center of each implant's base spanned the transcutaneous junction and extended above the skin, where it was covered by a protective hemi-spherical cap; see FIG. 2(a) for images of the implants and their orientation. After implant placement, each surgical site was irrigated with sterile saline and the incisions were closed using a layered approach, with absorbable sutures for the subcuticular layer and non-absorbable monofilament to close the skin around the columnar portion of each implant.

All rabbits received antibiotics and anti-inflammatory drugs at one hour pre-surgery, and b.i.d. for 24 hours post-surgery. Pain medication was administered immediately post-wound closure, and again at 12 hours post-surgery. The skin sutures were removed at 10 days post-surgery. Two rabbits each were randomly selected to be sacrificed at one, two, three and seven weeks post-surgery. Implants, surrounding skin, and subcutaneous tissues were harvested and processed for histological and histomorphometric analyses in order to quantify the degree of in-growth and to evaluate the relative tissue health and immune responses in and around the implant site.

Figure 3:
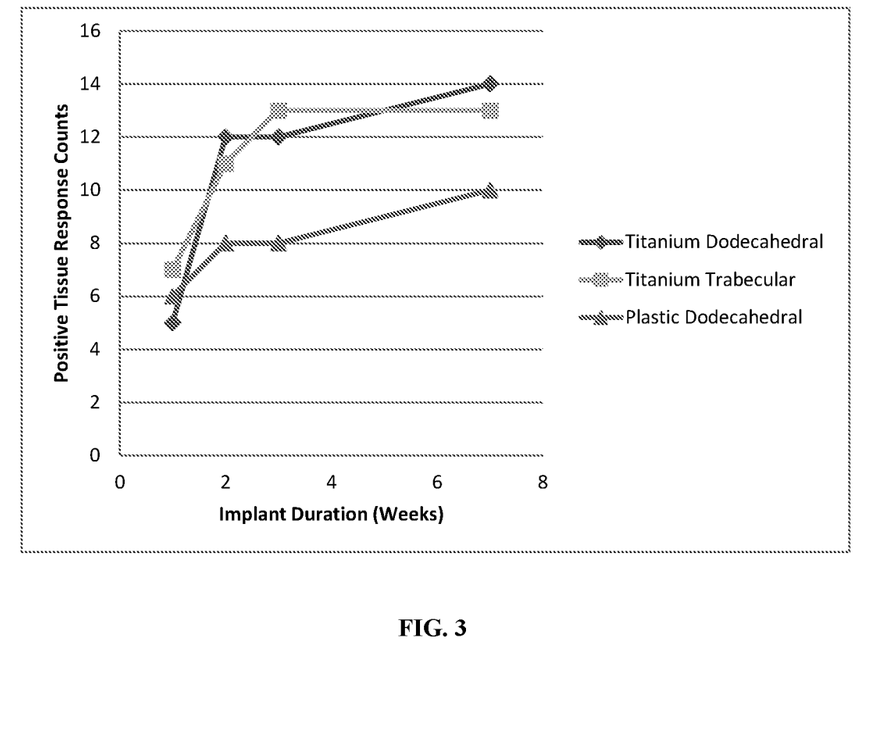
FIG. 3 shows positive response counts for soft tissue formation within pores, neovascularization, tissue differentiation/maturity, soft tissue healing and fibroconnective tissues as a function of implant duration for the titanium dodecahedral porous implants, titanium trabecular porous implants, and plastic dodecahedral porous implants.
Figure 4:
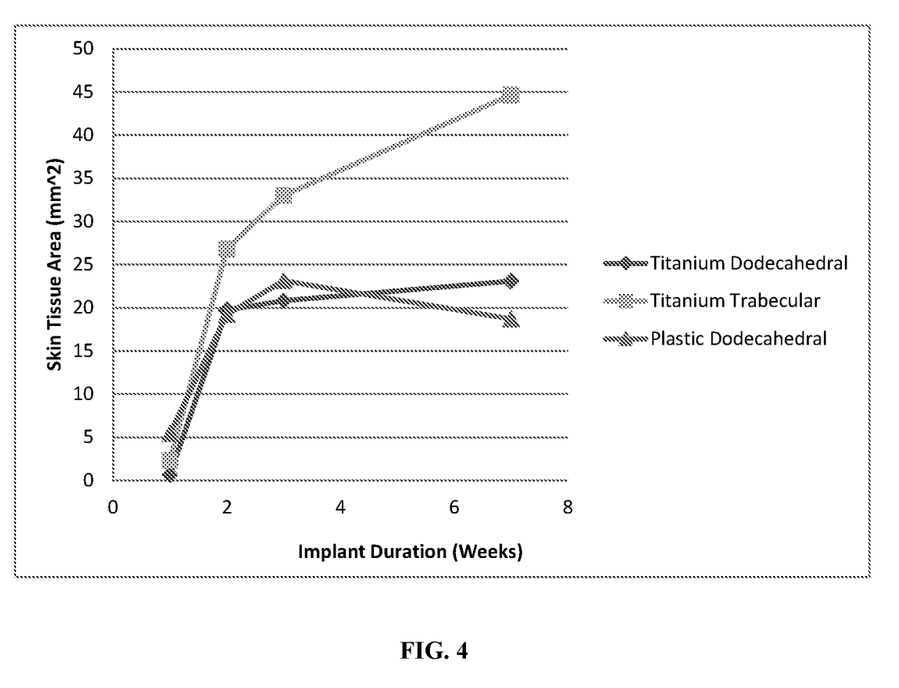
FIG. 4 shows skin tissue in-growth as a function of implant duration for titanium dodecahedral implants, titanium trabecular porous implants, and plastic dodecahedral porous implants.
Figure 5:
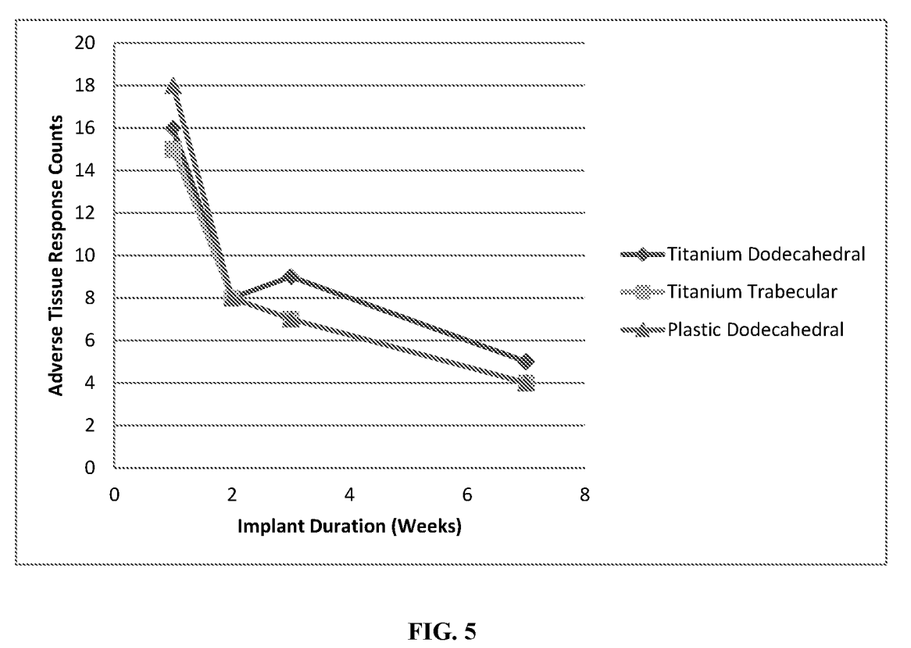
FIG. 5 shows adverse tissue responses including necrosis, inflammation/bacteria, fibrinous exudate, tissue degeneration, hemorrhages and fluid accumulation within pores as a function of implant duration for the titanium dodecahedral porous implants, titanium trabecular porous implants, and plastic dodecahedral porous implants.

Histology and histomorphometry were performed by AccelLAB (Quebec, Canada). Soft tissue was processed by a plastic resin-embedding and grinding system (Exakt Micro Grinding System), in which a cut was made along the center longitudinal axis of the implants. Each half was microground and polished to 20-60 µm in thickness. Sections were stained with hematoxylin and eosin (H&E) for analysis. Digital imaging analysis was utilized for documentation purposes at both low and high magnification. Histomorphometry was performed by digital analysis using Aperio ImageScope software or Image Pro Plus. Cell types and responses were evaluated utilizing a scoring system, provided by AccelLab, as shown in Tables 1 and 2.

tiation/maturation, and the formation of soft tissue within the implants increased with implant duration, as evident in FIG. 3. Furthermore, dermal in-growth was promoted by all implants and the magnitude of dermal in-growth into the porous network increased with implantation time, as demonstrated by FIG. 4. Negative tissue responses such as necrosis, infection/bacteria, fibrinous exudate, tissue degeneration, and hemorrhaging were observed, however the extent of adverse tissue effects decreased with increasing implant duration as seen in FIG. 5.

Figure 6:
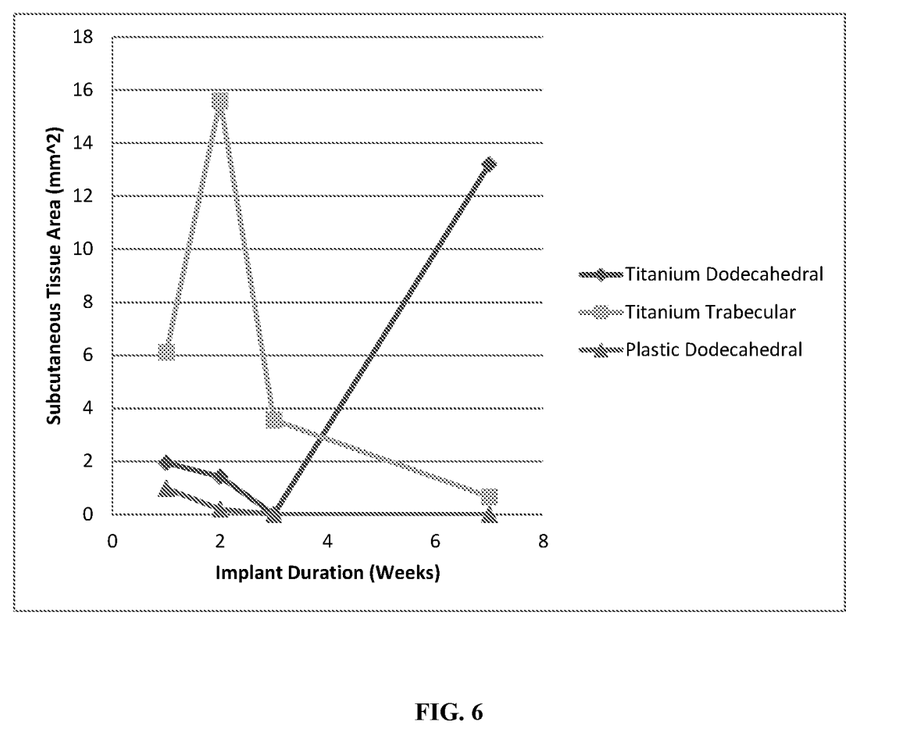
FIG. 6 shows subcutaneous tissue in-growth as a function of implant duration for the titanium dodecahedral porous implants, titanium trabecular porous implants, and plastic dodecahedral porous implants.
Figure 7:
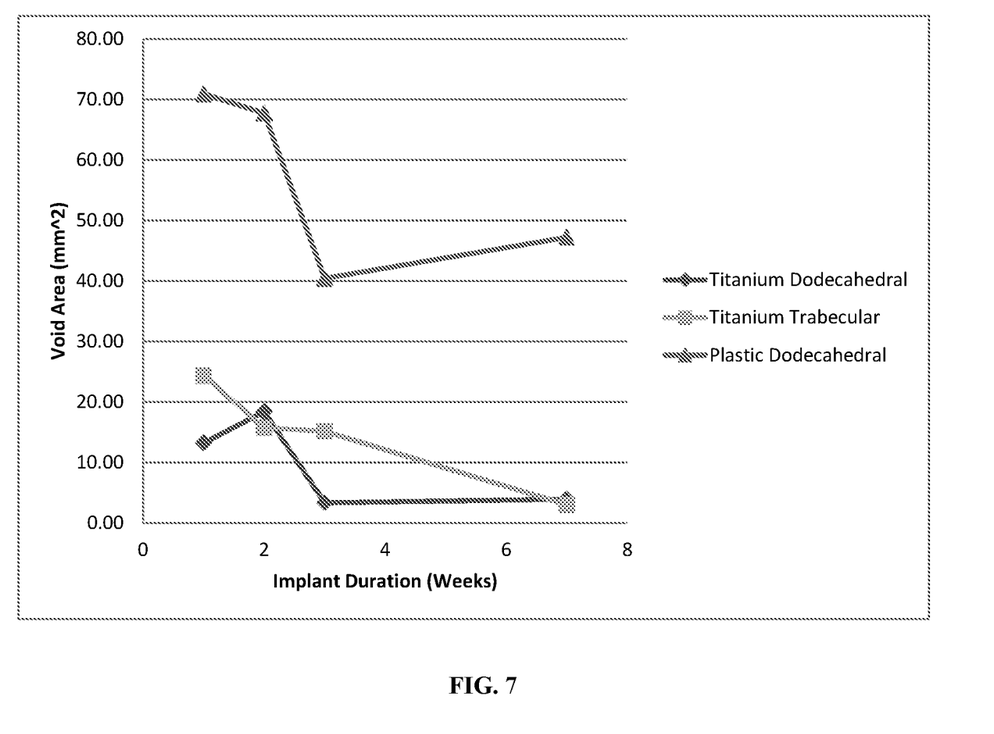
FIG. 7 shows total void area within the implants as a function of implant duration for the titanium dodecahedral implants, titanium trabecular porous implants, and plastic dodecahedral porous implants.
Figure 8:
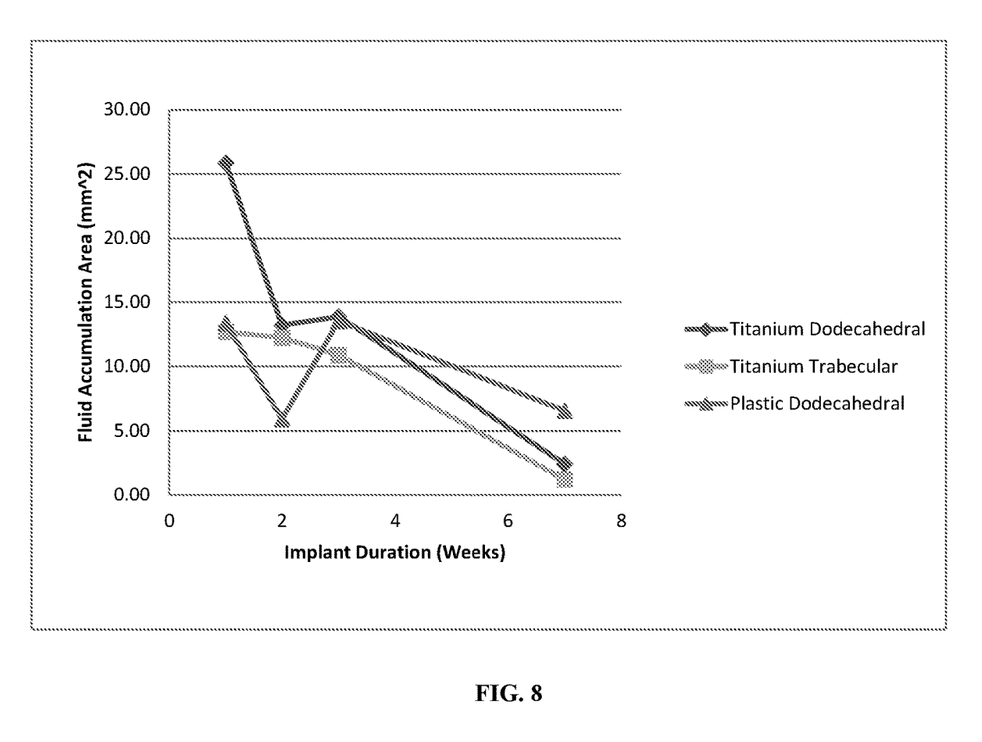
FIG. 8 shows fluid accumulated within the pore networks as a function of implant duration for the titanium dodecahedral porous implants, titanium trabecular porous implants, and plastic dodecahedral porous implants.
Figure 9:
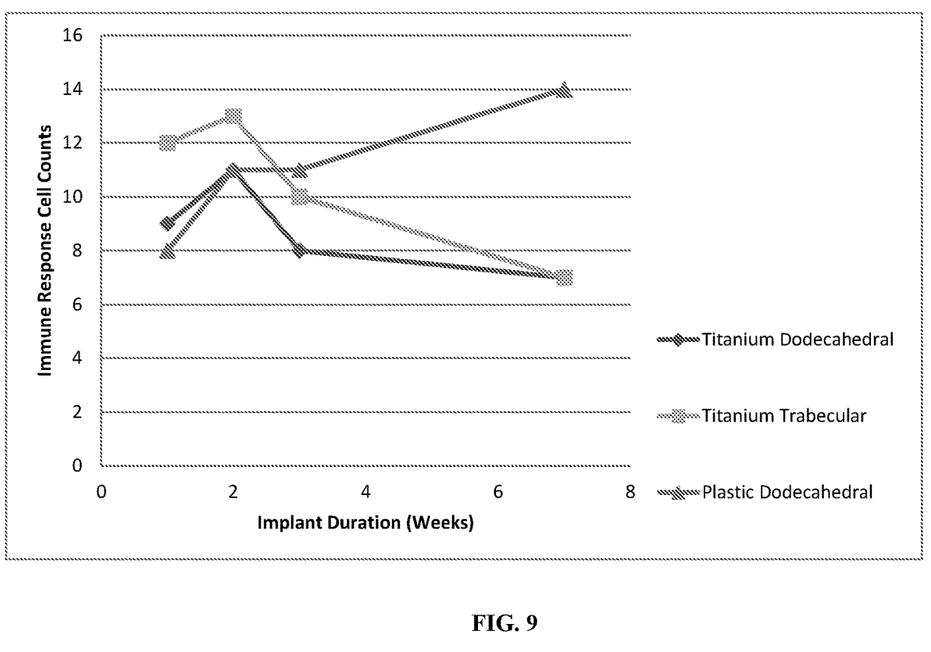
FIG. 9 shows immune response cell counts, including polymorphonuclear cells, lymphocytes, plasma cells, macrophages and giant cells as a function of implant duration for the titanium dodecahedral porous implants, titanium trabecular porous implants, and plastic dodecahedral porous implants.

Soft tissue in-growth was not entirely dependent upon material, as both the plastic and titanium implants promoted both skin and granular tissue in-growth. However, histomorphometry demonstrated that the magnitude of subcutaneous tissue in-growth for the plastic implants was minimal in comparison to the titanium implants, and actually decreased as implant duration increased, as shown in FIG. 6. A decrease in void area as implant duration increased was observed for all implants, however the void areas in the plastic implants were larger in magnitude than in titanium implants, see FIG. 7. Furthermore, fluid accumulation within the porous networks decreased as implant duration increased for both plastic and titanium implants, as evident in FIG. 8. Immune responses, including the presence of polymorphonuclear cells, lymphocytes, plasma cells, macrophages, and giant cells were evaluated through histology; immune responses decreased with increasing implant duration for the titanium implants, but increased for the plastic implants, see FIG. 9.

Histology and histomorphometry demonstrated that soft tissue in-growth into both plastic and titanium implants with a dodecahedral porous geometry was successful, although titanium implants were superior with respect to void area,

TABLE 1

Cell Type and Response Scoring System

| Cell Type/Response | Score | | | | |
|---|---|---|---|---|---|
| | 0 | 1 | 2 | 3 | 4 |
| Polymorphonuclear cells | 0 | Rare, 1-5/phf* | 6-10/phf | Heavy infiltrate | Packed |
| Lymphocytes | 0 | Rare, 1-5/phf* | 6-10/phf | Heavy infiltrate | Packed |
| Plasma cells | 0 | Rare, 1-5/phf* | 6-10/phf | Heavy infiltrate | Packed |
| Macrophages | 0 | Rare, 1-5/phf* | 6-10/phf | Heavy infiltrate | Packed |
| Giant cells | 0 | Rare, 1-2/phf* | 3-5/phf | Heavy infiltrate | Sheets |
| Necrosis | 0 | Minimal | Mild | Moderate | Severe |
| Infection/bacteria | 0 | Minimal | Mild | Moderate | Severe |
| Fibrinous exudate | 0 | Minimal | Mild | Moderate | Severe |
| Tissue degeneration | 0 | Minimal | Mild | Moderate | Severe |
| Neovascularisation | 0 | Minimal capillary proliferation focal, 1-3 buds | Groups of 4-7 capillaries with supporting fibroblastic structures | Broad band of capillaries with supporting structures | Broadband of capillaries with supporting structures |
| Fibrocytes/fibroconnective tissue, fibrosis | 0 | Narrow band | Moderately thick band | Thick band | Extensive band |
| Fatty infiltrate | 0 | Minimal amount of fat associated with fibrosis | Several layers of fat and fibrosis | Elongated and broad accumulation of fat cells about the implant site | Extensive fat completely surrounding the implant |

TABLE 2

Tissue Differentiation and Maturity Scoring System
Tissue Differntiation and Maturity
Score

| 0 | 1 | 2 | 3 | 4 |
|---|---|---|---|---|
| Hemorrhages and fibrin | hemorrhages, fibrin and granulation tissue | 2 = mostly granulation tissue with some hemorrhages and skin (epidermis/dermis/subcutis) | 3 = mostly skin (epidermis/dermis/subcutis) with some granulation tissue | relatively normal skin/subcutaneous tissue |

Results

Figure 2:
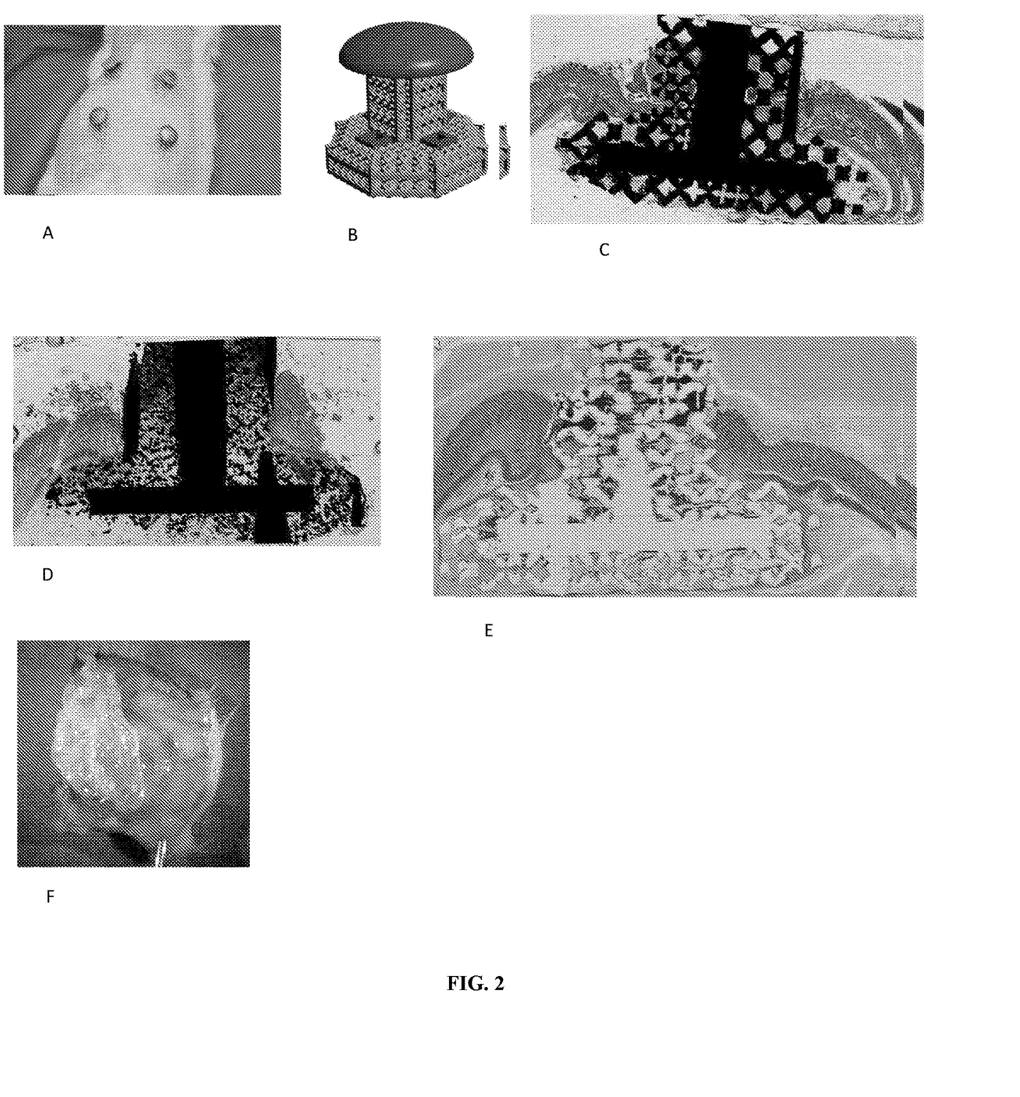
FIG. 2A-F show A) Implant orientation after sacrifice. B) Computer rendered image of the dodecahedral implant structure utilized for both plastic and titanium devices C) H&E stain of the titanium dodecahedral porous implant after an implantation time of 7 weeks. D) H&E stain of the titanium trabecular porous implant after an implantation time of 2 weeks. E) H&E stain of the plastic dodecahedral implant after an implantation time of 3 weeks. F) Image of a plastic dodecahedral porous implant post-harvest, inverted to show the base plate surrounded by vascularized tissue after an implantation time of 1 week

Qualitative and histological analysis showed that all implants had a significant degree of soft tissue in-growth, with vascularization plainly visible, see FIG. 2(b,c,d,e) for representative images. No evidence of infection was evident upon inspection for any rabbit throughout the study, and all rabbits displayed normal behavior and healthy feeding. Histology demonstrated that evidence of infection and bacteria were not found within subcutaneous implant sections. Minimal infection and bacteria was present at the dermal layer for implants harvested at 1, 2, and 3 weeks, however all indications of infection and bacteria at the dermal layer were absent by week 7. Neovascularization, tissue differenimmune response, and the magnitude of subcutaneous tissue in-growth. Soft tissue in-growth into the dodecahedral pore geometry titanium implants and the trabecular pore geometry titanium implants was similarly successful, although differences were clear in the amount of dermal and subcutaneous tissue in-growth. Subcutaneous tissue in-growth achieved a maximum value by week 2 for the trabecular pore geometry titanium implant, with 15.59 mm$^2$ of subcutaneous tissue present within the porous network (7.8% of total implant area), in-growth then decreased to a minimum value of 0.66 mm$^2$ (0.4% of total area) by week 7. Conversely, subcutaneous tissue in-growth into the dodecahedral pore geometry titanium implant exhibited a continually increasing trend, reaching 13.20 mm$^2$ (8% of total implant area) by week 7. Histomorphometry demonstrated that the trabecular pore geometry titanium implant was more successful at promoting dermal tissue in-growth than the dodecahedral pore geometry titanium implant. Specifically, dermal in-growth for the trabecular pore geometry implant reached a maximum value of 44.65 mm$^2$ (28.3% of total implant area) by week 7. Dermal in-growth for the dodecahedral pore titanium implant reached a maximum of 23.08 mm$^2$ (14.0% of total implant area) by week 7.

DISCUSSION

All rabbits in the present study were healthy throughout the implant trial with no visible signs of infection or implant rejection. Implants constructed of both plastic and titanium were found to have neovascularized tissue, as well as varying degrees of tissue differentiation and maturity ranging from mostly granular tissue to the in-growth of healthy skin and subcutaneous tissue. While there were no visible signs of infection or rejection during the study, histopathology revealed minimal infection and bacteria present in tissue that had proliferated into the pore networks at the dermal level for implant durations of 1-3 weeks. The dermal layers of the implants were however devoid of bacteria and infection by week 7. Subcutaneous sections of the implants were bacteria and infection free for all implants and all implantation times. Analysis of harvested implants after an implantation time of one week revealed significant skin in-growth. The rapid dermal in-growth may be the reason for the lack of foreign bacteria and other pathological material in the subcutaneous tissue. Previous studies have shown subcutaneous tissue in-growth occurs within four weeks of implantation; the present study demonstrated that provided implants allow for dermal tissue in-growth occurs much faster. Additionally, necrosis, tissue degeneration, hemorrhages and fibrinous exudate counts were lower in the subcutaneous tissue sections surrounding the implant than in sections at the level of the dermal layer. Without wishing to be held to a particular theory, it is hypothesized that if there was no dermal in-growth facilitated by the implants, the rabbits may have developed a bacterial infection, indeed such infections are commonly seen for transcutaneous implants, even with the use of antibiotics.

While immune response counts, skin tissue in-growth, and the total amount of fluid accumulated within the porous networks were similar for both the titanium dodecahedral porous implants and the plastic dodecahedral porous implants, the extent of subcutaneous tissue in-growth was larger in magnitude for the titanium dodecahedral porous implants. Indeed, the plastic dodecahedral porous implants did not facilitate significant subcutaneous tissue in-growth. As such, the total void area within the plastic dodecahedral porous implants was larger than within the titanium dodecahedral porous implants. Additionally, the positive tissue response counts for the plastic dodecahedral porous implants were consistently lower than those of the titanium dodecahedral porous implants. With regard to tissue differentiation and maturity, the titanium dodecahedral porous implant was populated with well developed skin and subcutaneous tissue by week 7, while the plastic dodecahedral porous implants contained mostly granulation tissue with hemorrhaging and a minimal amount of skin tissue by week 7. The formation of fibroconnective tissue was promoted by both the plastic and titanium dodecahedral porous implants, although the plastic dodecahedral porous implants showed narrow bands of fibrconnective tissue, with no further increase in connective tissue thickness as implant duration increased. Conversely, the titanium dodecahedral porous implants showed an increase in connective tissue thickness as a function of implantation time, achieving thick bands of fibroconnective tissue by week 7. The differences observed between the titanium dodecahedral porous implant and the plastic dodecahedral porous implant in facilitating differentiated and mature subcutaneous, skin, and connective tissue in-growth demonstrates an effect of implant material on the promotion of specific tissue types.

In this Example, the titanium trabecular and the titanium dodecahedral porous implants had comparable immune response counts, positive response counts, adverse tissue effects, void areas, and total fluid accumulation within the porous networks. Subcutaneous tissue in-growth for the titanium trabecular porous implant was observed to increase to a maximum by week 2, and then decrease to a minimum value close to that of the plastic dodecahedral porous implant by week 7, suggesting that a trabecular pore geometry is not ideal for the promotion of subcutaneous tissue in-growth. Conversely, the titanium trabecular porous implant was the most successful at facilitating dermal in-growth, the titanium dodecahedral porous were significantly less successful, showing that dermal in-growth is more dependent on pore geometry than implant material. Additionally, the titanium trabecular porous implant was populated by thick bands of fibroconnective tissue by week 3, an observation not made for the titanium dodecahedral porous implant until week 7.

This Example provides the first known demonstration that porous, transcutaneous implants of varying material and pore geometry, created by additive manufacturing, are biocompatible and able to facilitate the in-growth of a variety of tissue types, including fibroconnective, dermal and subcutaneous tissue. Rapid skin tissue in-growth protected subcutaneous sections of the implant from bacteria and pathogenic material, resulting in no need for long term antibiotics. Applications utilizing transcutaneous implants of a porous nature are far reaching, and include, inter alia, potential uses in prosthetics and surgery in sensitive areas such as hip and knee replacements.

We claim:
1. An implant comprising
a biocompatible substrate including a first layer and a second layer, wherein said first layer comprises a plurality of pores, and said second layer comprises a plurality of pores, wherein the pores of said first layer have geometries that are different than the pores of said second layer, and wherein said implant is configured as a transcutaneous implant to remain in the skin and to facilitate skin tissue and/or subcutaneous tissue ingrowth.

2. The implant of claim 1, wherein the pores of said first layer are regular and/or substantially uniform in at least one of size and shape.

3. The implant of claim 2, wherein said regular and/or substantially uniform pores are dodecahedral.

4. The implant of claim 1, wherein the pores of said second layer are regular and/or substantially uniform in at least one of size and shape.

5. The implant of claim 1, wherein the pores of said first layer are irregular.

6. The implant of claim 1, wherein the pores of said second layer are irregular.

7. The implant of claim 6, wherein said irregular pores exhibit a trabecular or substantially trabecular geometry.

8. The implant of claim 1, wherein said pores of said first layer are between 1-5,000 µm in diameter.

9. The implant of claim 1, wherein said pores of said second layer are between 1-5,000 µm in diameter.

10. The implant of claim 1, wherein the substrate comprises titanium, tantalum, a polymer, or a ceramic material.

11. The implant of claim 1, wherein the substrate is coated with one or more growth factors.

* * * * *